United States Patent
Kloas et al.

(10) Patent No.: US 8,291,640 B2
(45) Date of Patent: Oct. 23, 2012

(54) AQUAPONIC SYSTEM FOR VEGETABLE AND FISH PRODUCTION

(75) Inventors: Werner Kloas, Berlin (DE); Bernhard Rennert, Berlin (DE); Christoph Van Ballegooy, Berlin (DE); Manfred Drews, Grossbeeren (DE)

(73) Assignee: Forschungsverbund Berlin E. V., Berlin (DE)

( * ) Notice: Subject to any disclaimer, the term of this patent is extended or adjusted under 35 U.S.C. 154(b) by 73 days.

(21) Appl. No.: 12/808,421

(22) PCT Filed: Oct. 27, 2008

(86) PCT No.: PCT/EP2008/064546
§ 371 (c)(1),
(2), (4) Date: Aug. 10, 2010

(87) PCT Pub. No.: WO2010/022800
PCT Pub. Date: Mar. 4, 2010

(65) Prior Publication Data
US 2011/0131880 A1    Jun. 9, 2011

(30) Foreign Application Priority Data

Aug. 28, 2008  (EP) .................................. 08163189

(51) Int. Cl.
*A01G 31/00* (2006.01)
(52) U.S. Cl. ........................................ 47/62 R
(58) Field of Classification Search .................. 47/62 R, 47/62 A, 62 C, 17
See application file for complete search history.

(56) References Cited

U.S. PATENT DOCUMENTS

| 5,046,451 A | 9/1991 | Inslee |
| 5,200,033 A * | 4/1993 | Weitzman ............ 159/47.1 |
| 2005/0102851 A1* | 5/2005 | He et al. ............ 34/92 |

FOREIGN PATENT DOCUMENTS

| DE | 240327 A1 | 10/1986 |
| EP | 1112680 A | 7/2001 |
| JP | 2001-190166 A | 7/2001 |

OTHER PUBLICATIONS

International Search Report Dated Mar. 30, 2009.

* cited by examiner

*Primary Examiner* — Monica Williams
(74) *Attorney, Agent, or Firm* — Norris Mclaughlin & Marcus P.A.

(57) ABSTRACT

The invention relates to an aquaponic facility with closed water circulation, including at least one aquaculture unit and at least one hydroponic unit, characterized in that the aquaculture unit has at least one water outlet which is functionally connected with the hydroponic unit by a one-way valve such that water from the aquaculture unit can be supplied to the hydroponic unit, and the hydroponic unit has at least one cold trap, wherein the at least one cold trap is functionally connected with the aquaculture unit in such a way that the water obtained from the at least one cold trap can be supplied to the aquaculture unit, as well as its use.

13 Claims, 2 Drawing Sheets

AQUAPONIC SYSTEM FOR VEGETABLE AND FISH PRODUCTION

This application is a 371 application of PCT/EP2008/064546 filed Oct. 27, 2008, which claims priority to the European application 08163189.7 filed Aug. 28, 2008.

TECHNICAL FIELD

The present invention relates to an aquaponic facility with closed water circulation, a method for producing aquaponic products, and the use of an aquaponic facility.

TECHNICAL BACKGROUND AND STATE-OF-THE-ART

The term aquaculture refers to the controlled breeding of aquatic organisms, such as for example fish, crustaceans, mussels, or water plants, such as algae. The aquaculture and the aquaculture technology are a strongly developing market worldwide. At this time, approximately 29% of the worldwide fishery harvest is met by products from aquaculture.

An inherent problem with aquaculture is that in the course of breeding, the water is contaminated by metabolites from the animals, for example from the fish, and/or by residues from the added feedstock, and must hence be purified so that the breeding productivity is not at risk.

This is accomplished in so-called open aquaculture systems by replacing the water with fresh water and discharging the used water into the environment. This severely pollutes the environment and can cause eutrophication and even hypertrophication of existing natural bodies of water. In addition, the water consumption of such systems is very high. This increases the costs of such systems, so that they can only be operated at locations with sufficient water resources.

In order to minimize these disadvantages, aquaculture systems with closed water circulation has been developed where the used or waste water is reprocessed through combined mechanical-biological water purification and returned to the pisciculture.

Various biological filters are used in the biological purification. In these filters, the nitrogen compounds excreted by the fish, in particular ammonium and/or ammonia, are oxidized to nitrate by bacterial nitrification. In a closed circulation system, the nitrification process causes a decrease in the pH value accompanied by nitrate accumulation in the treated water. This process can be contravened either by using a denitrification stage or by adding more fresh water. In both situations, unused nitrogen is released into the environment. However, this nitrogen, in particular nitrogen from the nitrate, can be readily used for supplying nutrients to plants. For this reason, attempts have been made in the past for a combined fish and plant production with the goal of an improved nutrient utilization and water purification. So-called aquaponic facilities were created, wherein a hydroponic culture (or hydro-culture), which absorbs the nitrate-containing water after nitrification, was integrated in a closed-loop aquaculture system. The nitrate-containing effluent from the aquaculture is here supplied in a hydroponic culture as nutrient solution to the plants. The water containing the nitrate that is not taken up by the plants is returned to the aquaculture. The plants thus operate as nitrate recipients. Suitable aquaponic facilities are described, for example, in the patent DD 240 327 A1 and by Rennert and Drews, 1989 (B. Rennert, M. Drews; Eine Möglichkeit der kombinierten Fisch- und Gemüseproduktion in Gewächshäusern (*A possibility for combined fish and vegetable production in greenhouses*); Fortschr. Fisch.wiss. 8 (1989): 19:27).

One problem with these systems is that the water for the breeding animals of the aquaculture and the water for the plants of the hydroponic culture have different requirements. While plants require in the root area a pH value of less than 6, before they can grow successfully, fish require a pH value of greater than 6 before they can be produced cost-effectively. While the nitrate-containing water, in the form it exists from the biological filter, meets the pH value required for the plants, the water to be returned to the aquaculture contains still too much residual nitrate and does not have the required pH value beneficial for fish. In conventional aquaponic facilities, the required pH value compensation was essentially achieved by adding fresh water. Overall, the fresh water required in the aquaponic facility for adjusting the pH value and for preventing accumulation of nitrate in the treated water was on average about 20 to 25% of the total water volume of the system per day (Rennert and Drews 1989). Such high water consumption allows a cost-effective operation of aquaponic facilities only with high-priced fish, and the location of such system is limited to areas with an adequate water supply.

It is therefore an object of the present invention to lessen or eliminate the aforementioned disadvantages of the current state-of-the-art.

Solution According to the Invention

The object is solved by providing an aquaponic facility with closed water circulation, having at least one aquaculture unit and at least one hydroponic unit, characterized in that the aquaculture unit has at least one water outlet which is functionally connected via a one-way valve with the hydroponic unit such that water from the aquaculture unit can be supplied to the hydroponic unit, and the hydroponic unit has at least one cold trap, wherein the at least one cold trap is functionally connected with the aquaculture unit in such a way that the water obtained from the at least one cold trap can be supplied to the aquaculture unit.

In the aquaponic facility according to the invention, the used water of the aquaculture unit flows through a water outlet via a one-way valve to the hydroponic unit, where the water is used to water the plants and supply the plants with nutrients. The plants absorb the water and the nutrients (among others, nitrate) and then release through plant transpiration water without nutrients (among others, nitrate) into the air in the hydroponic unit. This transpiration water from the plants is collected by the cold trap of the hydroponic unit and returned to the aquaculture unit. A closed water circulation is created in the aquaponic facility, wherein the plants of the hydroponic unit serve as natural filter for nitrate and as natural corrective measure for the pH value of the water. The plants are not only the recipient of the nitrate contained in the water, but operate as genuine nitrate filter by releasing transpiration water that is essentially free of nitrate. It is hence no longer necessary to add fresh water for regulating the pH value or the nitrate concentration in the treated water before returning the treated water to the aquaculture unit. Water is removed from the aquaponic facility of the invention only by removing biomass in form of breeding animals and plant material, so that only this water needs to be supplied during operation of the system. In a preferred embodiment, an aquaponic facility of the invention can thereby be provided where the required daily supply of fresh water during operation of the system is less than 5% of the total water volume of the system, most preferably less than 3%.

Accordingly, the aquaponic facility of the invention provides for the first time a closed, almost emission-free system where essentially only fish food and very small amounts of water need to be introduced. The system of the invention can thus be operated more environmentally friendly and at lower-cost and can also be used in areas where little water is available.

The term "aquaculture unit" in the context of the present invention refers to a system that is suitable for the controlled breeding of aquatic organisms, such as fish, crustaceans, mussels and water plants, for example algae. Such aquaculture systems are known in the art and have been described in the literature.

In a preferred embodiment, the aquaculture unit has at least one area for breeding fish (pisciculture), for example in form of a fish breeding tank, pond or trough, a mechanical filter and a biological filter.

Suitable mechanical filters are used to absorb suspended particles, for example excrements and uneaten food components, from the waste water. The sediment produced in the mechanical filter can be removed from the mechanical filters. Suitable conventional mechanical filters are known to a skilled artisan. Examples for suitable mechanical filters are mechanical filters such as lamellae separators, micro-sieves, and sedimentation tanks. Lamellae separators are preferred.

Suitable biological filters are preferably used for nitrification, i.e., oxidation of ammonium/ammonia to nitrate by way of nitrite. Either chemical methods or microorganisms are used for the nitrification. Preferably, autotrophic bacteria are used, particularly preferred are bacteria of the species *nitrosomonas* and *nitrobacter*. In addition, suitable filters can have a heterotrophic area where carbon degradation occurs and carbon dioxide is released. When using submerged biological filters, a large portion of the generated carbon dioxide remains in the circulating water. For this reason, biological filters in form of percolating filters are preferred, where the produced carbon dioxide can be released from the percolating filter in form of gas and does not remain in the circulating water. In one embodiment of the aquaponic facility of the invention, the carbon dioxide gas released from the percolating filter is supplied to the hydroponic unit. A skilled artisan is familiar with suitable conventional biological filters. Preferably, a percolating filter is used as the biological filter.

The aquaculture unit is functionally connected with the hydroponic unit via a one-way valve, so that water from the aquaculture unit can be supplied to the hydroponic unit. Suitable one-way valves are used to control the discharge from the aquaculture unit and/or the supply into the hydroponic unit. The suitable one-way valve according to the invention is constructed so as to allow water flow essentially only in one direction, from the aquaculture unit into the hydroponic unit. The one-way valves can be regulated and/or controlled either manually or automatically; they can optionally be controlled by a computer. In addition, each valve is configured and controllable to allow water flow essentially only in one direction. A skilled artisan is familiar with suitable conventional one-way valves. A skilled artisan will know that the capacity of the one-way valves should be adapted to the overall size of the aquaponic facility to permit a smooth operation of the facility. In a preferred embodiment, the aquaculture unit has more than one one-way valve. By taking into consideration the overall size of the system, a skilled artisan can then readily provide the adequate capacity for water discharge and supply and thereby ensure a particularly advantageous operation of the facility. In a preferred embodiment, the one-way valve is a magnetic valve. The one-way valve can be controlled, for example, by a float-switch located in the nutrient tank of the hydroponic unit. When the water level in the tank with the nutrient solution decreases, for example as a result of water absorption by the plants, the one-way valve opens and water is added from the fish circulation into the hydroponic unit. Water flow in the opposite direction is prevented.

The term "hydroponic unit" in the context of the present invention refers to a system that is configured for plant breeding (horticulture) and plant growth, where the plants take roots, instead of in soil containing organic substances, in an inorganic substrate or without any substrate commensurate with the so-called nutrient film technique (NFT, see for example Graves, C. J. (1993): The nutrient film technique. Horticult Rev, 5, 1-44). Nutrients are supplied to the plants through an aqueous solution of inorganic mineral nutrients. The hydroponic unit according to the invention includes by definition always at least one greenhouse in which the horticulture is housed. In one embodiment of the aquaponic facility, in which both the aquaculture unit and the hydroponic unit are arranged in a common greenhouse, the greenhouse of the hydroponic unit is simultaneously the greenhouse which includes both the aquaculture unit and the hydroponic unit. In a preferred embodiment of the aquaponic unit, the hydroponic system has at least one area for preparing and/or storing the nutrient solution, for example a nutrient solution tank to which optionally additional nutrients or supplements can be admixed, and one area for horticulture. The skilled artisan is familiar with suitable conventional hydroponic units, for example from Rennert and Drews (1989) or from the patent DD 240 327 A1.

The aquaponic facility according to the invention includes a hydroponic system having at least one cold trap. Suitable cold traps are used to condense and collect water from the air of the hydroponic unit or from the air space of the combined hydroponic and aquaculture unit. Corresponding cold traps and cold trap technique are known to the skilled artisan. Fundamentally, any cold trap can be used for the aquaponic facility of the invention. A skilled artisan will also know that for a smooth operation of the system, the capacity of the cold trap(s) should be matched to the overall size of the aquaponic facility. In a preferred embodiment, the hydroponic unit has more than one cold trap, wherein the cold traps can be arranged side-by-side and/or sequentially. By taking into consideration the overall size of the system, a skilled artisan can then readily provide an adequate capacity of cold trap activity and ensure a particularly beneficial operation of the system.

In a preferred embodiment of the aquaponic facility, both the aquaculture unit and the hydroponic unit are functionally arranged in a common greenhouse, creating a common continuous air space which is connected with the at least one cold trap of the hydroponic unit. With this arrangement, the cold trap can not only recover the transpiration water of plants from the air space, but can also condense and collect the evaporated water from the aquaculture unit. The water loss during the operation of the system is thereby further reduced compared to conventional systems.

The aquaponic facility of the invention can in addition include a photovoltaic system. The photovoltaic system is configured for suitable absorption of solar energy and conversion of the solar energy into electric energy. Suitable photovoltaic systems are known in the art. The photovoltaic system can be installed, depending on the location of the system and the available space, on the roof of the greenhouse or as an open space system. The suitable photovoltaic system provides electric current for the operation of the at least one cold trap of the hydroponic unit. When selecting a suitable photovoltaic system, the skilled artisan considers the overall size of the aquaponic facility and configures the size of the photovoltaic system commensurate with the expected power consumption of the cold trap(s) of the hydroponic unit. Excess energy from the photovoltaic system can optionally be used for regulating the water temperature of the aquaculture unit.

The aquaponic facility of the invention can include a biogas system. Suitable biogas systems are capable of producing biogas from biomass and generate electric energy from the produced biogas. The biogas system of the aquaponic facility of the invention can be operated with the sediment from the mechanical filter of the aquaculture unit as well as with fish and plant waste. The electric energy from the biogas system can be used for operating to cold trap(s) of the hydroponic unit, but also for operating the temperature control for the water of the aquaculture unit.

In a particularly preferred embodiment of the aquaponic facility, the aquaculture unit is operated with fish meal and/or fish-oil-free feedstock. Preferably, feedstock is used where the fish meal is completely substituted by fly larvae meal and the fish oil by plant oil.

In another preferred embodiment, the aquaculture unit is operated with fish, preferably tilapias, preferably with *oreochromis niloticus*. These fish are particularly suitable for the aquaculture because they easily reproduce regardless of the season, are resistant against elevated water temperatures (above 30° C.) which may occur during the summer months in greenhouses, and have in addition very few bones and are full of flavor.

The hydroponic unit of the aquaponic facility according to the invention is preferably operated with vegetable plants, particularly preferred with tomatoes (e.g., *solanum lycopersicum*) and/or cucumbers (e.g., *cucumis sativus*). The hydroponic unit of the aquaponic facility of the invention can also be operated with other plants besides vegetable plants. Particularly suitable are always those plants that are distinguished by a particularly a high absorption and processing capability for nitrates, such as *ceratophyllum demersum* (common chickweed), basil (*ocimum basilicum*), okra (*abelmoschus esculentus*) and various lettuce plants.

A skilled artisan is aware that different factors must be considered when sizing the aquaponic facility of the invention in order to obtain optimal results. For example, the selection of the type of fish and the quantity of fish of the aquaculture unit together with the total water volume of the aquaponic facility has a certain influence on how the hydroponic unit must be operated and sized in order to attain a particularly beneficial operating result. Other factors, such as the water temperature and the environment, the average exposure time to light and the light intensity at different times must also be considered. All these factors are not only determined by the selection of the fish for the aquaponic unit and the selection of the plants for the hydroponic unit, but they also depend on the selection of the location and the overall size of the system. A skilled artisan will readily take the aforedescribed effects into account when planning and constructing the aquaponic facility of the invention, and arrive at a functional aquaponic facility according to the invention having the aforedescribed advantages. For example, the operation of the aquaculture unit can be started up with a larger quantity of fish by operating the hydroponic unit with plants that have particularly high capacity for nitrate absorption and processing.

According to another aspect, the invention relates to a method for operating an aquaponic facility which is characterized in that:

a) water from an aquaculture unit is supplied to a hydroponic unit via a water outlet having a one-way valve;

b) the water is absorbed by plants of the hydroponic unit and released through plant transpiration into the atmosphere of the hydroponic unit;

c) the water is collected from the atmosphere of the hydroponic unit through condensation; and d) the collected water is returned to the aquaculture unit.

The water from the atmosphere of the hydroponic unit can be condensed by any suitable method; preferably, however, one or more cold traps are used.

In a preferred embodiment of the method, the aquaculture unit is operated with fish meal and/or fish-oil-free feedstock.

In an embodiment of the method of the invention, the aquaculture unit is operated with tilapias, preferably with *oreochromis niloticus*.

In another embodiment of the method of the invention, the hydroponic unit is operated with vegetable plants, preferably with tomatoes and/or cucumbers.

The invention also relates to a method for producing aquaculture products, such as fish, crustaceans, mussels or water plants, for example algae, and/or of hydroponic products, for example vegetables, such as tomatoes and/or cucumbers, wherein an aquaponic facility according to the invention is used.

The invention also relates to the use of an aquaponic facility according to the invention for producing aquaculture and/or hydroponic products.

FIGURES

EXEMPLARY EMBODIMENTS

Figure 1:
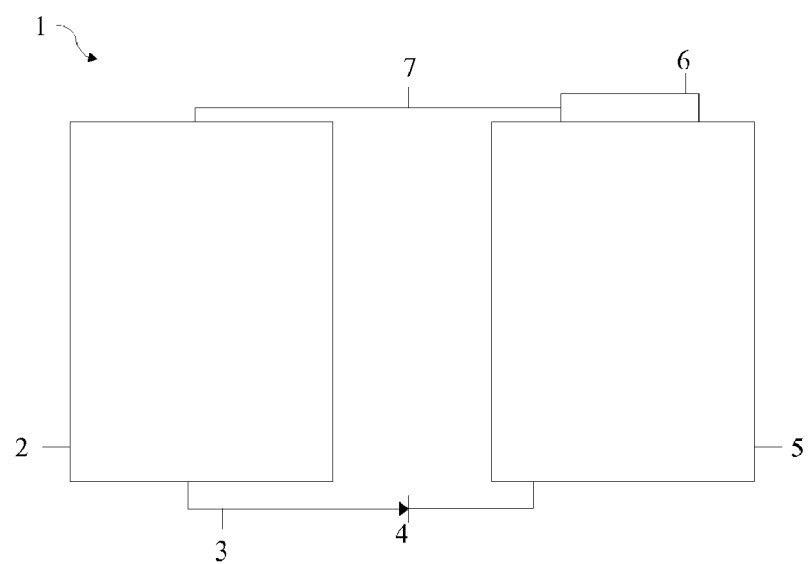
FIG. 1 shows an embodiment of the aquaponic facility according to the invention.

FIG. 1 shows an exemplary embodiment of an aquaponic facility 1 according to the invention. The aquaponic facility 1 includes an aquaculture unit 2 which is connected with a hydroponic unit 5 via a water outlet 3 having a one-way valve 4. The hydroponic unit 5 includes a cold trap 6 which is connected with the aquaculture unit 2 by way of a return flow 7. The used from the aquaculture unit 2 is supplied via the water outlet 3 through the one-way valve 4 to the hydroponic unit 5, where the water including the nitrates and other nutrients is absorbed by the plants. The plants release the water in form of plant transpiration again into the ambient air of the hydroponic unit 5. This water is condensed from the ambient air by the cold trap 6 and collected. The treated water is then returned from the cold trap 6 to the aquaculture unit 2 via the return flow 7. This closes the water circulation loop.

Figure 2:
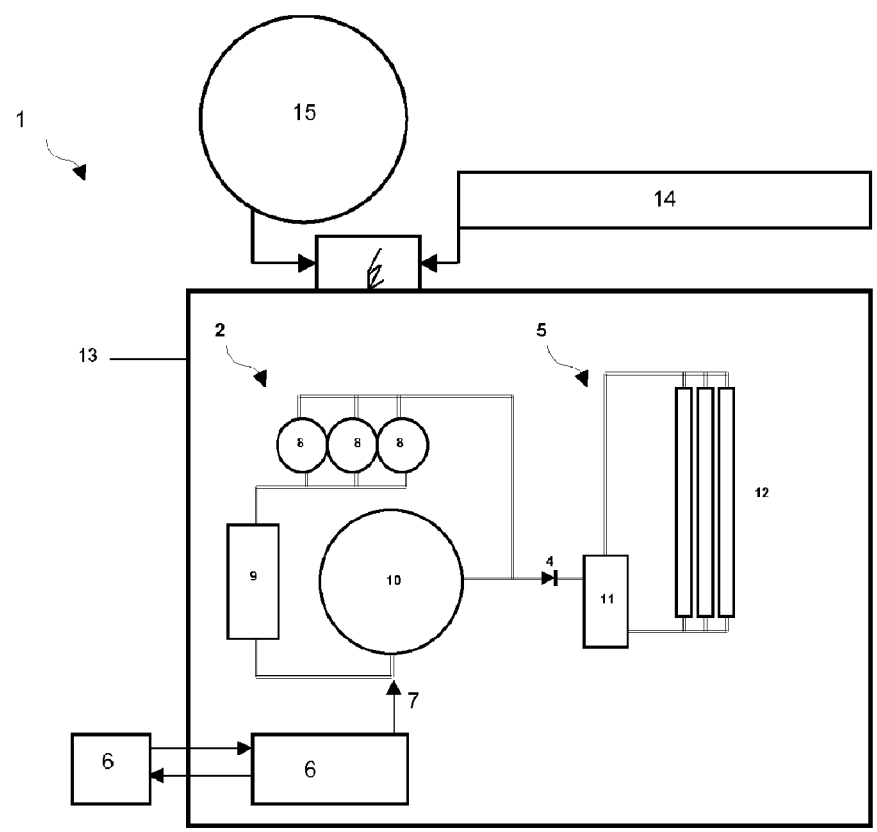
FIG. 2 shows another embodiment of the aquaponic facility according to the invention, with a common greenhouse with an aquaculture and a hydroponic unit, as well as a climate control unit with cold trap, a photovoltaic system and a biogas system.

FIG. 2 shows another exemplary embodiment of an aquaponic facility according to the invention. In addition to the embodiment of FIG. 1, additional components of the aquaculture unit and the hydroponic unit are illustrated. In this embodiment, the aquaculture unit 2 and the hydroponic unit 5 are located in a common greenhouse 13. The used water from the fish breeding tanks 8 is supplied to a mechanical filter 9 which mechanically sediments suspended matter from the water. Thereafter, the purified water is supplied from the mechanical filter 9 to the biological filter 10. The nitrification takes place in the biological filter under formation of carbon dioxide. The water which now contains nitrate, is transported, for example as needed, from the aquaculture unit 2 to the hydroponic unit 5 via the one-way valve 4, where it enters the nutrient solution tank 11, optionally adding supplements or nutrients. Thereafter, the water is supplied to the planter boxes 12, where the water including the nitrates and other nutrients is absorbed by the plants. Water, including nitrates that are not absorbed, is supplied to the nutrient solution tank 11. The plants again release water in form of plant transpiration into the ambient air of the hydroponic unit 5. The water is condensed from the ambient air by the cold trap 6 and collected. The treated water is then returned from the cold trap 6 via the return flow 7 to the aquaculture unit 2, thereby closing the water circulation loop. In this embodiment, energy is commonly supplied by the photovoltaic system 14 and the biogas system 15.

LIST OF REFERENCES SYMBOLS

1 Aquaponic facility
2 Aquaculture unit
3 Water outlet
4 One-way valve
5 Hydroponic unit
6 Cold trap, optionally coupled with climate control
7 Return flow
8 Fish breeding tank
9 Mechanical filter
10 Biological filter
11 Nutrient solution tank
12 Planter boxes
13 Greenhouse
14 Photovoltaic system
15 Biogas system

The invention claimed is:

1. Aquaponic facility (1) with closed water circulation, comprising at least one aquaculture unit (2) and at least one hydroponic unit (5), wherein the aquaculture unit (2) has at least one water outlet (3) which is functionally connected via a one-way valve (4) with the hydroponic unit (5) such that water from the aquaculture unit (2) can be supplied to the hydroponic unit (5), and the hydroponic unit (5) has at least one cold trap (6), wherein the at least one cold trap (6) is functionally connected with the aquaculture unit (2) in such a way that the water obtained from the at least one cold trap (6) can be supplied to the aquaculture unit (2).

2. Aquaponic facility (1) according to claim 1, wherein the hydroponic unit (5) has more than one cold trap (6), wherein the cold traps (6) are arranged side-by-side and/or sequentially.

3. Aquaponic facility (1) according to claim 1, wherein the one-way valve (4) is configured for manual or automatic control.

4. Aquaponic facility (1) according to claim 1, wherein the hydroponic unit (5) has at least one area for the preparation and/or storage of the nutrient solution (11) and one area for horticulture.

5. Aquaponic facility (1) according to claim 1, wherein the aquaculture unit (2) has at least one area for pisciculture (8), a mechanical filter (9) and a biological filter (10).

6. Aquaponic facility (1) according to claim 1, wherein the aquaculture unit (2) and the hydroponic unit (5) are functionally arranged in a common greenhouse such that a common continuous air space is created which is connected with the at least one cold trap (6) of the hydroponic unit (5).

7. Aquaponic facility (1) according to claim 1, wherein the daily supply of fresh water during operation of the facility is less than 5% of the total water volume of the facility.

8. Aquaponic facility (1) according to claim 1, wherein the aquaponic facility (1) additionally comprises a photovoltaic system.

9. Aquaponic facility (1) according to claim 1, wherein the aquaponic facility (1) comprises a biogas system.

10. Method for operating an aquaponic facility (1), comprising the steps of:
a) supplying water from an aquaculture unit (2) to a hydroponic unit (5) via a water outlet (3) having a one-way valve (4);
b) following absorption of the water by plants of the hydroponic unit (5) and release of the water through plant transpiration into the atmosphere of the hydroponic unit, collecting the water from the atmosphere of the hydroponic unit (5) through condensation; and
c) returning the collected water to the aquaculture unit (2).

11. Method according to claim 10, wherein the aquaculture unit (2) is operated with fish meal and/or fish-oil-free feedstock.

12. Method according to claim 10, wherein the aquaculture unit (2) is operated with tilapias, preferably with oreochromis niloticus.

13. Method according to claim 10, wherein the hydroponic unit (5) is operated with vegetable plants, preferably with tomatoes and/or cucumbers.

* * * * *